(12) United States Patent
Welser

(10) Patent No.: US 9,669,201 B2
(45) Date of Patent: Jun. 6, 2017

(54) APPLICATOR FOR USE WITH OINTMENT AND METHOD OF USE

(71) Applicant: Jennifer Welser, New York, NY (US)

(72) Inventor: Jennifer Welser, New York, NY (US)

( * ) Notice: Subject to any disclaimer, the term of this patent is extended or adjusted under 35 U.S.C. 154(b) by 504 days.

(21) Appl. No.: 14/224,926

(22) Filed: Mar. 25, 2014

(65) Prior Publication Data
US 2014/0205359 A1 Jul. 24, 2014

Related U.S. Application Data

(63) Continuation of application No. 12/777,889, filed on May 11, 2010, now Pat. No. 8,708,980.

(51) Int. Cl.
| | | |
|---|---|---|
| *A61M 35/00* | (2006.01) | |
| *B65D 5/72* | (2006.01) | |
| *B43K 5/00* | (2006.01) | |
| *B43M 11/06* | (2006.01) | |
| *A61F 9/00* | (2006.01) | |

(52) U.S. Cl.
CPC ......... *A61M 35/003* (2013.01); *A61F 9/0026* (2013.01); *A61M 35/00* (2013.01); *A61F 2250/0067* (2013.01); *A61F 2250/0068* (2013.01)

(58) Field of Classification Search
CPC ................. A61M 35/003; A61M 35/00; A61F 2250/0068; A61F 2250/0067; A61F 9/0026
USPC ..... 604/2, 310, 289; 401/156, 209, 183, 202
See application file for complete search history.

(56) References Cited

U.S. PATENT DOCUMENTS

| | | | |
|---|---|---|---|
| 886,984 A | 5/1908 | Joplin | |
| 2,715,980 A * | 8/1955 | Frick ...................... | B65D 49/08 137/853 |
| 3,141,579 A | 7/1964 | Medlock | |
| 3,669,323 A | 6/1972 | Harker et al. | |
| 4,105,142 A | 8/1978 | Morris, Jr. | |
| 4,747,521 A | 5/1988 | Saffron | |
| 5,067,638 A | 11/1991 | Bavaveas | |
| 5,330,081 A | 7/1994 | Davenport | |
| 5,584,420 A | 12/1996 | Awada et al. | |
| 6,330,960 B1 | 12/2001 | Faughey et al. | |
| 6,537,260 B1 * | 3/2003 | Lamb .................... | A61M 31/00 604/279 |
| 2004/0011830 A1 | 1/2004 | Kim | |
| 2009/0188950 A1 | 7/2009 | Gaus et al. | |

(Continued)

*Primary Examiner* — Jacqueline Stephens
(74) *Attorney, Agent, or Firm* — Lathrop & Gage L.L.P.

(57) ABSTRACT

One applicator for use with ointment includes a housing defining a holding chamber. The holding chamber has a single entrance distinct from a single exit and is flexible such that deformation of the housing reduces capacity of the holding chamber and forces contents of the holding chamber to pass through the exit. A one-way valve is at the entrance for allowing the ointment to enter the holding chamber through the entrance and restricting the ointment from exiting the holding chamber through the entrance. A tip extends from the housing adjacent the exit. The tip has a proximal end meeting the housing and a pliant distal end spaced apart from the housing. The tip distal end is flared from the tip proximal end and has a generally planar leading surface. A channel in the tip extends from the exit to the leading surface, and is flared at the leading surface.

18 Claims, 3 Drawing Sheets

(56) References Cited

U.S. PATENT DOCUMENTS

2012/0093567 A1* 4/2012 Kravchenko ........ A45D 40/262
401/143

* cited by examiner

APPLICATOR FOR USE WITH OINTMENT AND METHOD OF USE

RELATED APPLICATIONS

This application is a continuation of U.S. patent application Ser. No. 12/777,889, filed May 11, 2010, the disclosure of which is incorporated by reference in its entirety herein.

BACKGROUND

The invention relates generally to the field of applicators. More particularly, the invention relates to the field of applicators for use with ointment, such as ophthalmic ointment, for example.

In both the human and veterinary medical fields, ophthalmic medications are typically applied in either a solution or ointment form. There are advantages and disadvantages to each. Solutions can be more easily applied with a controlled drop dose, but they are frequently more irritating and have less contact time with the eye (requiring more frequent dosing). Depending on the medication, solutions also tend to be more expensive. Ointments have better contact time, are generally more soothing, and can typically be used less frequently. However, they can be more difficult to apply, and controlling dosage can be a problem. Any excessive ointment applied, while often not harmful, can be messy and bothersome; this can cause patients to rub the eyes more, and can make it increasingly difficult to keep the eye area clean. Ointments are typically applied from metal tubes having a metal or hard plastic tip that easily gets coated and greasy with excess ointment. Contamination of the tube tip is a concern, and there is no way to regulate the amount of medication dispensed from the tube.

SUMMARY

An applicator for use with ointment according to one embodiment includes a housing defining a holding chamber. The holding chamber has a single entrance and a single exit, and the exit is distinct from the entrance. The housing is flexible such that deformation of the housing reduces capacity of the holding chamber and forces contents of the holding chamber to pass through the exit. A one-way valve is at the entrance for allowing the ointment to enter the holding chamber through the entrance and restricting the ointment from exiting the holding chamber through the entrance. A tip extends from the housing adjacent the exit. The tip has a proximal end meeting the housing and a pliant distal end spaced apart from the housing. The tip distal end is flared from the tip proximal end and has a generally planar leading surface. A channel in the tip extends from the exit to the leading surface, and the channel is flared at the leading surface.

According to another embodiment, an applicator for use with ointment includes a housing defining a holding chamber. The holding chamber has a single entrance and a single exit and being otherwise enclosed; the exit is distinct from the entrance. The housing is flexible such that deformation of the housing reduces capacity of the holding chamber and forces contents of the holding chamber to pass through the exit. Means are included for restricting ointment from passing from the holding chamber through the entrance. A tip extends from the housing adjacent the exit. The tip has a proximal end meeting the housing and a pliant distal end spaced apart from the housing. The tip distal end is flared from the tip proximal end and has a leading surface. A channel extends in the tip from the exit to the leading surface.

DETAILED DESCRIPTION

Figure 1:
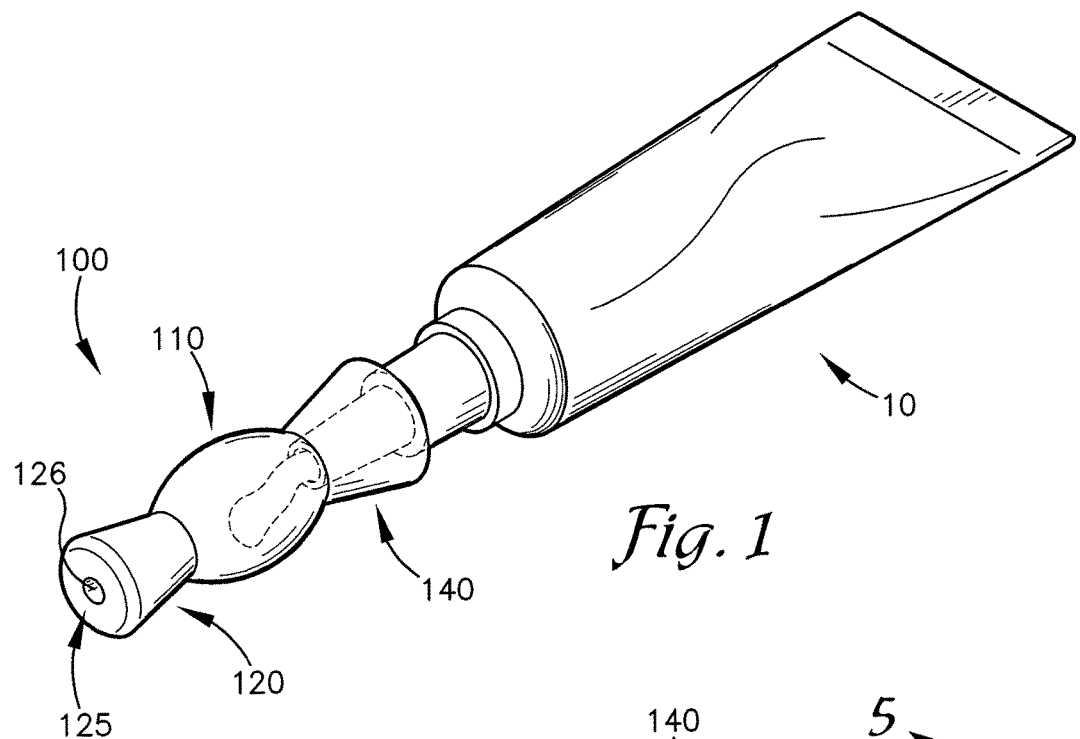
FIG. 1 shows a perspective view of an applicator, according to one embodiment, in use with a tube of ointment.
Figure 2:
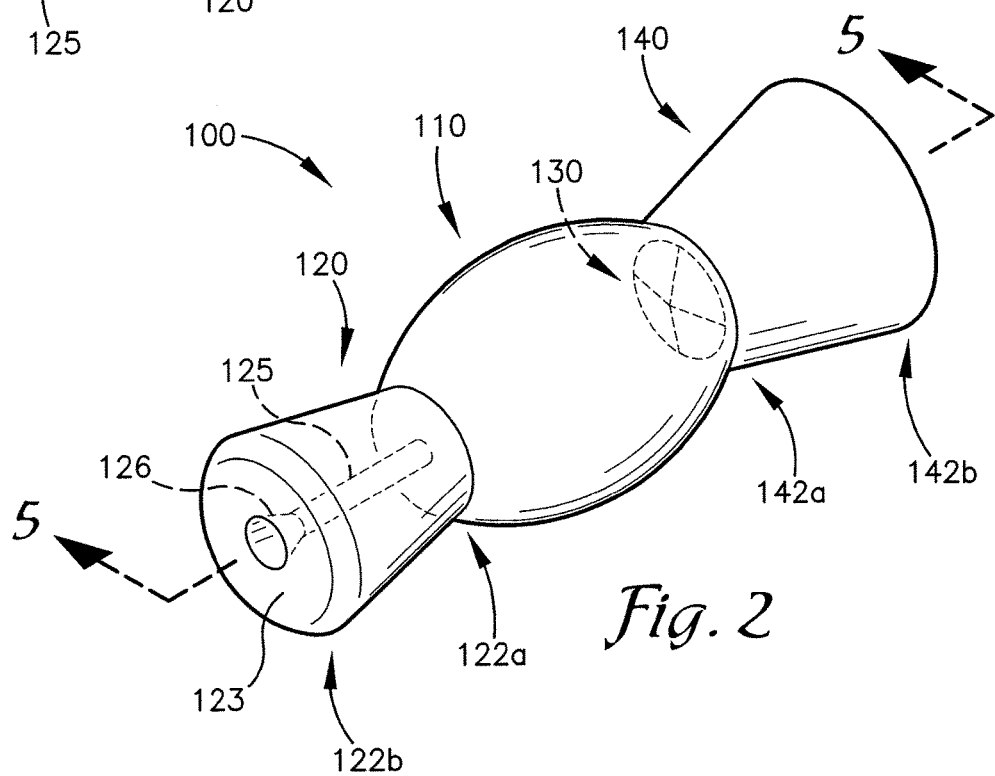
FIG. 2 shows another perspective view of the applicator of FIG. 1, with internal features in dashed lines.
Figure 3:
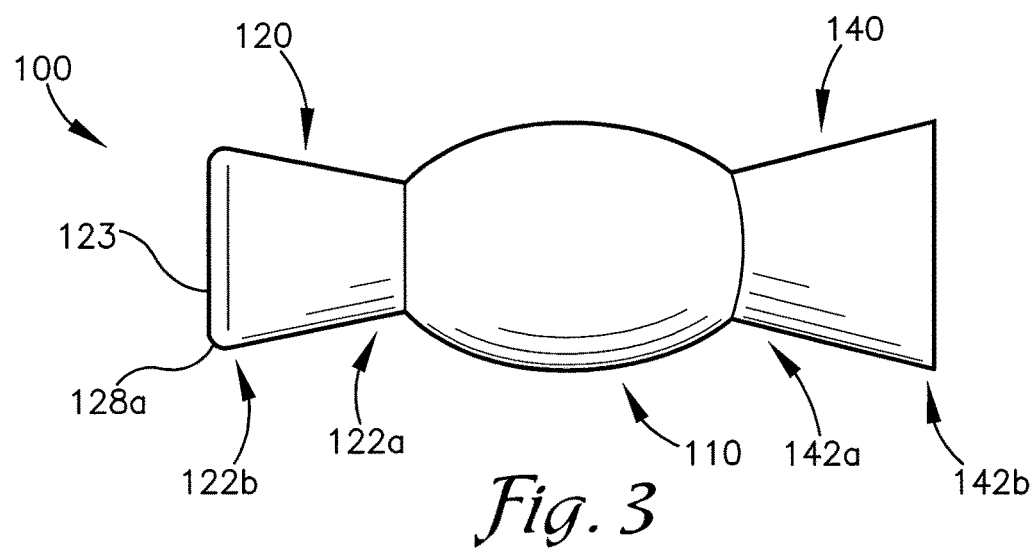
FIG. 3 shows a side view of the applicator of FIG. 1.
Figure 4:
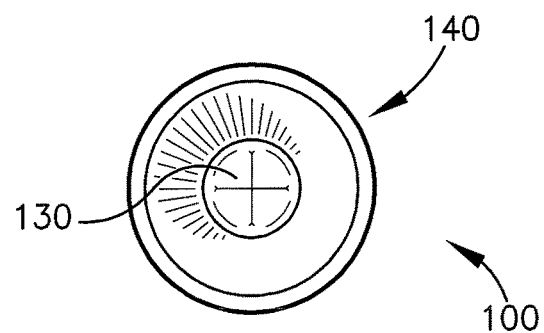
FIG. 4 shows an end view of the applicator of FIG. 1.

Detailed descriptions of various embodiments are set forth herein to enable those skilled in the art to practice the current invention. Referring now to the drawings, FIGS. 1 through 5 show an applicator 100 according to one embodiment of the present invention. The applicator 100 includes a housing 110 defining a holding chamber 112.

Figure 5:
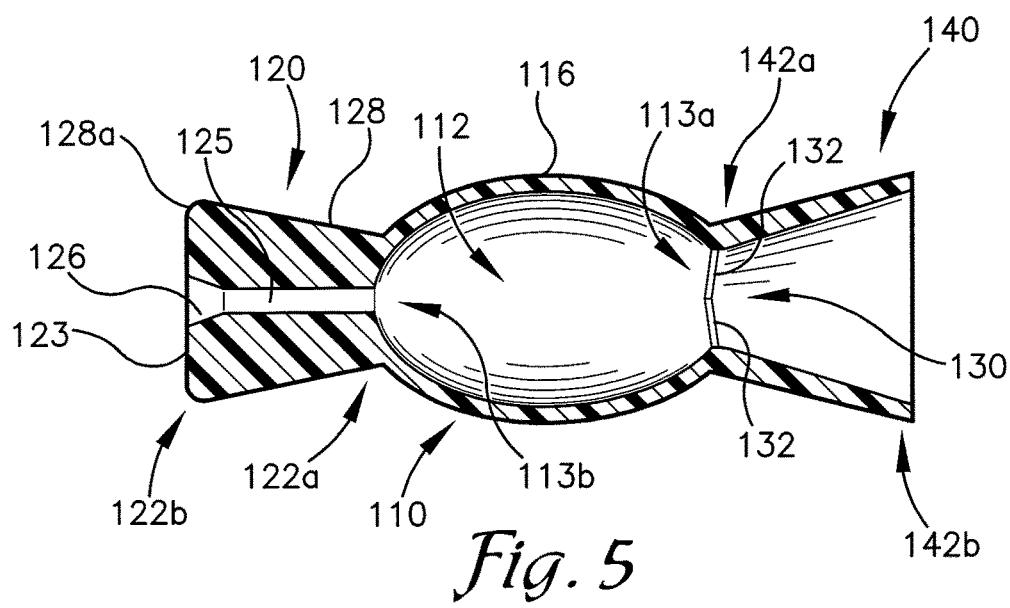
FIG. 5 shows a sectional view of the applicator of FIG. 1, taken from FIG. 2.

As shown in FIG. 5, the holding chamber 112 has a single entrance 113a, a single exit 113b distinct from the entrance 113a, and may be otherwise enclosed (e.g., by sidewall 116). The housing 110 is flexible such that deformation of the housing 110 reduces capacity of the housing 110 and forces contents of the holding chamber 112 (e.g., air, ointment, etc.) to pass through the exit 113b. As discussed further below, the holding chamber 112 may have a volume generally equal to a single ointment dose, and the housing 110 may be transparent such that contents of the holding chamber 112 are viewable through the housing 110.

A tip 120 extends from the housing 110 adjacent the exit 113b, as shown throughout the drawings. The tip 120 has a proximal end 122a meeting the housing 110 and a pliant distal end 122b spaced apart from the housing 110. The tip distal end 122b is flared from the tip proximal end 122a and may have a generally planar leading surface 123. A channel 125 (FIGS. 2 and 5) in the tip 120 extends from the exit 113b to the leading surface 123 and is flared 126 at the leading surface 123.

It may be desirable for the entrance 113a, the exit 113b, and the channel 125 to be collinear, such as shown in FIG. 5. Further, the tip 120 has (or is defined by) a sidewall 128 extending between the tip proximal end 122a and the tip distal end 122b, and in some embodiments the sidewall 128 has a rounded portion 128a meeting the leading surface 123. While it may be desirable for the thickness of the housing 110 at the holding chamber 112 (e.g., the thickness of the sidewall 116) to be less than the thickness of the tip sidewall 128, the thickness of the tip sidewall 128 may nevertheless be sufficiently small (and the channel 125 may be sufficiently narrow) such that the channel 125 is collapsible.

Means are included for restricting ointment from passing from the holding chamber 112 through the entrance 113a. For example, a one-way valve 130 (FIGS. 2, 4, and 5) may be at the entrance 113a for allowing ointment to enter the holding chamber 112 through the entrance 113a and restricting the ointment from exiting the holding chamber through the entrance 113a. The one-way valve 130 may have any acceptable known or later-developed configuration, such as (for example) a plurality of self-sealing flaps 132 that are angled (or "biased") inwardly (as shown) and/or that overlap.

In some embodiments, a sleeve 140 may be included, as shown throughout the drawings. The sleeve 140 extends from the housing 110 adjacent the entrance 113*a*. A proximal end 142*a* of the sleeve 140 meets the housing 110, and a distal end 142*b* of the sleeve 140 is spaced apart from the housing 110. The distal end 142*b* of the sleeve 140 may be flared from the sleeve proximal end 142*a*, and is hollow for receiving a tube 10 (FIG. 1) and allowing ointment to pass from the tube 10 to the holding chamber 112 through the entrance 113*a* (e.g., through the one-way valve 130). The housing 110, the tip 120, and the sleeve 140 may have a unitary construction (e.g., of medical grade silicone, soft plastic, or another appropriate material), or various portions may be coupled together.

To use the applicator 100, then, the holding chamber 112 is selected to have a volume generally equal to a single ointment dose, as noted above. An ointment (e.g., an ophthalmic ointment or other substance) is then inserted to the holding chamber 112 through the entrance 113*a* (e.g., through the one-way valve 130). This may be done by a manufacturer, or may be done by the user. Especially if the user fills the holding chamber 112 (e.g., from the tube 10), the sleeve 140 may be useful in guiding the tube 10 through the one-way valve 130 and the entrance 113*a*. And if the housing 110 is transparent, the user may visually determine when the holding chamber 112 has been filled. Further, when the tube 10 is removed, any stray or excess ointment on the tube 10 may be maintained inside the sleeve 140 instead of on the outside of the applicator 100 or the tube 10. The tube 10 may be recapped for future use, as it has not been contaminated through the applicator-filling process.

The filled applicator 100 may then be used to apply its contents. If the applicator 100 contains ophthalmic ointment, the pliant tip 120 may be put to the user's eye with the channel flare 126 toward the eye. The user's eyelid may be held open, and the channel flare 126 may be held near or touching the periphery of the eye. The housing 110 may be squeezed (i.e., deformed), forcing the ointment to pass through the exit 113*b* and the channel 125 and on the eye. If the ointment doesn't release from the tip 120, the tip 120 may be gently touched to the periphery of the eye. After the ointment is applied, the applicator 100 may be discarded or recycled. Any excess ointment may be maintained within the applicator 100 and not on the user.

While the applicator has been described in a situation where a user applies ointment to his own eye, it should be understood that one person may instead use the applicator 100 to apply ointment to another person or animal. The soft nature and configuration of the tip 120 may help prevent injury. Further, as noted above, using the applicator 100 may allow a desired amount of ointment to be applied, and also prevent the tube 10 from becoming contaminated. Those skilled in the art will also understand that, while the applicator 100 has been described in housing and applying ophthalmic ointment, other substances may alternately be used, such as dermatologic ointments, toothpaste, lotions, and particularly ointments and gels having a desired dosage amount and substances where contamination is a concern.

Figure 6:
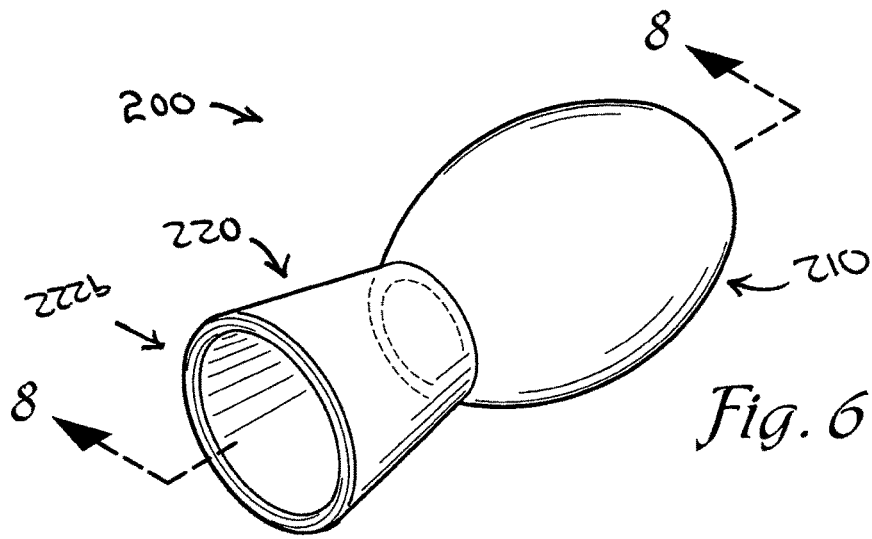
FIG. 6 shows a perspective view of an applicator, according to another embodiment.
Figure 7:
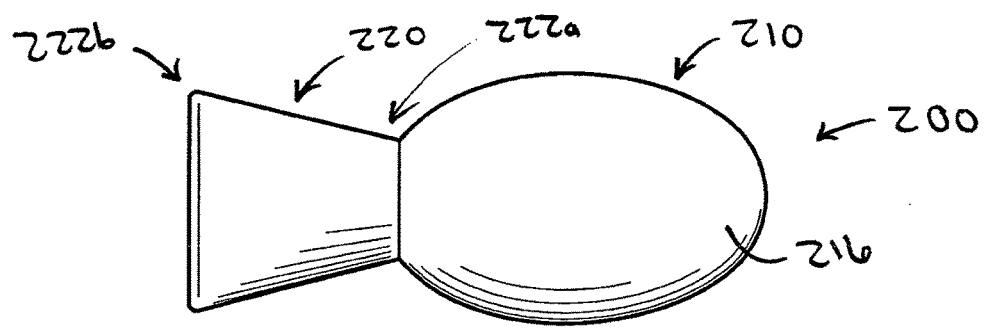
FIG. 7 shows a side view of the applicator of FIG. 6.
Figure 8:
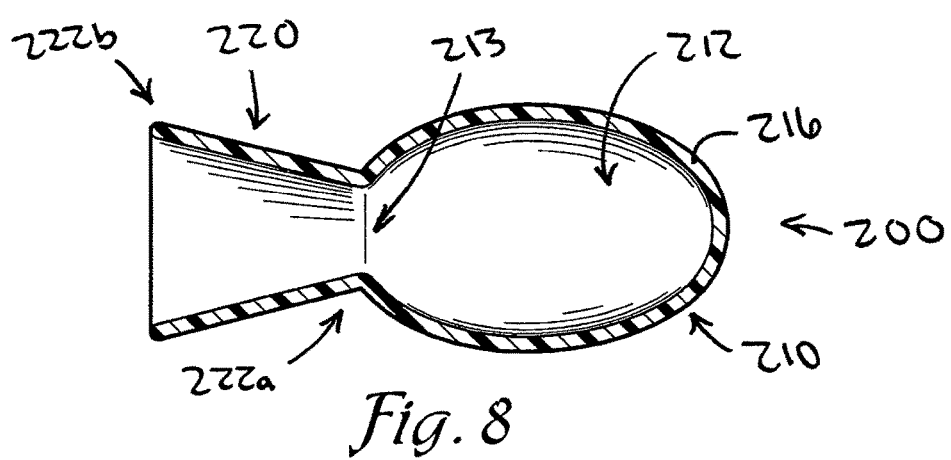
FIG. 8 shows a sectional view of the applicator of FIG. 6, taken from FIG. 6.

FIGS. 6 through 8 show an alternative embodiment 200 of the inventive applicator. The applicator 200 includes a housing 210 defining a holding chamber 212. As shown in FIG. 8, the holding chamber 212 has a single opening 213, and may be otherwise enclosed (e.g., by sidewall 216).

A tip 220 extends from the housing 210 adjacent the opening 213, as shown in the drawings. The tip 220 has a proximal end 222*a* meeting the housing 210 and a distal end 222*b* spaced apart from the housing 210. The tip distal ends 222*b* is flared from the tip proximal end 222*a*, and the tip 220 is hollow.

Many different arrangements of the various components depicted, as well as components not shown, are possible without departing from the spirit and scope of the present invention. Embodiments of the present invention have been described with the intent to be illustrative rather than restrictive. Alternative embodiments will become apparent to those skilled in the art that do not depart from its scope. A skilled artisan may develop alternative means of implementing the aforementioned improvements without departing from the scope of the present invention. Further, it will be understood that certain features and subcombinations are of utility and may be employed without reference to other features and subcombinations and are contemplated within the scope of the claims. Various steps set forth herein may be carried out in orders that differ from those set forth herein without departing from the scope of the present methods. The description should not be restricted to the above embodiments, but should be measured by the following claims.

I claim:

1. An ointment applicator, comprising:
   an ovoid housing defining a holding chamber;
   ointment in the holding chamber; and
   a tip extending from the ovoid housing; the tip having proximal end meeting the ovoid housing and a distal end spaced apart from the ovoid housing; the tip having a channel extending from the tip proximal end to the tip distal end and being in communication with the holding chamber; a cross-sectional area of the channel at the tip proximal end being less than a cross-sectional area of the channel at the tip distal end the channel being unimpeded from the holding, chamber to the tip distal end;
   wherein the ovoid housing is flexible such that deformation of the ovoid housing reduces capacity of the holding chamber and forces the ointment in the holding chamber to pass unimpeded through the tip channel; and
   wherein the tip channel comprises:
   a first generally cylindrical portion extending from the tip proximal end to an intermediate point; and
   a second frustoconical portion extending from the intermediate point to the tip distal end.

2. The ointment applicator of claim 1, wherein the tip has a generally frustoconical exterior configuration; the generally frustoconical exterior configuration having a generally planar leading surface and a sidewall; the leading surface being at the tip distal end and meeting the sidewall at a rounded corner.

3. The ointment applicator of claim 2, wherein the ointment is an ophthalmic ointment.

4. The ointment applicator of claim 3, wherein the ovoid housing and the tip are constructed of silicone.

5. The ointment applicator of claim 4, wherein the ovoid housing is transparent.

6. The ointment applicator of claim 1, wherein the ointment is an ophthalmic ointment.

7. The ointment applicator of claim 2, wherein the tip has a generally frustoconical exterior configuration rounded at the tip distal end.

8. An ointment applicator, comprising:
a housing defining a holding chamber;
ophthalmic ointment in the holding chamber; and
a tip extending from the housing; the tip having a proximal end meeting the housing and a distal end spaced apart from the housing; the tip being rounded at the distal end; the tip having a channel extending from the tip proximal end to the tip distal end and being in communication with the holding chamber; a cross-sectional area of the channel at the tip proximal end being less than a cross-sectional area of the channel at the tip distal end; the channel being unimpeded from the holding chamber to the tip distal end;
wherein the housing is flexible such that deformation of the housing reduces capacity of the holding chamber and forces the ointment in the holding chamber to pass unimpeded through the tip channel; and
wherein the tip channel comprises:
 a first generally cylindrical portion extending from the tip proximal end to an intermediate point; and
 a second frustoconical portion extending from the intermediate point to the tip distal end.

9. An ointment applicator, comprising:
a housing defining a holding chamber;
ophthalmic ointment in the holding chamber; and
a tip extending from the housing; the tip having a proximal end meeting the housing and a distal end spaced apart from the housing; the tip being rounded at the distal end; the tip having a channel extending from the tip proximal end to the tip distal end and being in communication with the holding chamber; a cross-sectional area of the channel at the tip proximal end being less than a cross-sectional area of the channel at the tip distal end; the channel being unimpeded from the holding chamber to the tip distal end;
wherein the housing is flexible such that deformation of the housing reduces capacity of the holding chamber and forces the ointment in the holding chamber to pass unimpeded through the tip channel;
wherein the tip channel comprises a frustoconical portion extending from the tip distal end; and
wherein the tip has a generally frustoconical exterior configuration; the generally frustoconical exterior configuration having a generally planar leading surface and a sidewall; the leading surface being at the tip distal end.

10. The ointment applicator of claim 9, wherein the tip channel frustoconical portion ends at an intermediate point; and the tip channel has a generally cylindrical portion extending from the intermediate point to the tip proximate end.

11. An applicator, comprising:
an ovoid housing defining a holding chamber;
a substance in the holding chamber; and
a tip extending from the ovoid housing; the tip having a proximal end meeting the ovoid housing and a distal end spaced apart from the ovoid housing; the tip having a channel extending from the tip proximal end to the tip distal end and being in communication with the holding chamber; a cross-sectional area of the channel at the tip proximal end being less than a cross-sectional area of the channel at the tip distal end; the channel being unimpeded from the holding chamber to the tip distal end;
wherein the ovoid housing is flexible such that deformation of the ovoid housing reduces capacity of the holding chamber and forces the substance in the holding chamber to pass unimpeded through the tip channel; and
wherein the tip channel comprises:
 a first generally cylindrical portion extending from the tip proximal end to an intermediate point; and
 a second frustoconical portion extending from the intermediate point to the tip distal end.

12. The applicator of claim 11, wherein the substance includes a medication.

13. The applicator of claim 11, wherein the tip has a generally frustoconical exterior configuration; the generally frustoconical exterior configuration having a generally planar leading surface and a sidewall; the leading surface being at the tip distal end and meeting the sidewall at a rounded corner.

14. The applicator of claim 11, wherein the ovoid housing and the tip are constructed of silicone.

15. The applicator of claim 11, wherein the ovoid housing is transparent.

16. The applicator of claim 11, wherein the tip has a generally frustoconical exterior configuration rounded at the tip distal end.

17. An applicator, comprising:
a housing defining a holding chamber;
a substance in the holding chamber; and
a tip extending from the housing; the tip having a proximal end meeting the housing and a distal end spaced apart from the housing; the tip being rounded at the distal end; the tip having a channel extending from the tip proximal end to the tip distal end and being in communication with the holding chamber; a cross-sectional area of the channel at the tip proximal end being less than a cross-sectional area of the channel at the tip distal end; the channel being unimpeded from the holding chamber to the tip distal end;
wherein the housing is flexible such that deformation of the housing reduces capacity of the holding chamber and forces the substance in the holding chamber to pass unimpeded through the tip channel;
wherein the tip channel comprises a frustoconical portion extending from the tip distal end; and
wherein the tip has a generally frustoconical exterior configuration; the generally frustoconical exterior configuration having a generally planar leading surface and a sidewall; the leading surface being at the tip distal end.

18. The applicator of claim 17, wherein the tip channel frustoconical portion ends at an intermediate point; and the tip channel has a generally cylindrical portion extending from the intermediate point to the tip proximate end.

* * * * *